(12) United States Patent
Kato et al.

(10) Patent No.: US 8,691,956 B2
(45) Date of Patent: Apr. 8, 2014

(54) MONOCLONAL ANTIBODY AGAINST HUMAN HIG-1 POLYPEPTIDE

(75) Inventors: Fuminori Kato, Kusatsu (JP); Yoshitaka Kondo, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 0 days.

(21) Appl. No.: 13/498,392

(22) PCT Filed: Sep. 29, 2010

(86) PCT No.: PCT/JP2010/066893
§ 371 (c)(1),
(2), (4) Date: Mar. 27, 2012

(87) PCT Pub. No.: WO2011/040429
PCT Pub. Date: Apr. 7, 2011

(65) Prior Publication Data
US 2012/0244560 A1    Sep. 27, 2012

(30) Foreign Application Priority Data
Sep. 30, 2009 (JP) ................................ 2009-226517

(51) Int. Cl.
*C07K 16/00* (2006.01)
*C07K 16/28* (2006.01)
*C12N 5/12* (2006.01)

(52) U.S. Cl.
USPC ..................... 530/388.2; 530/387.1; 435/326; 435/332; 435/810

(58) Field of Classification Search
None
See application file for complete search history.

(56) References Cited

U.S. PATENT DOCUMENTS

2003/0044862 A1   3/2003   Giaccia

FOREIGN PATENT DOCUMENTS

| JP | 2002-507405 A1 | 3/2002 |
| WO | WO 99/48916 A2 | 9/1999 |
| WO | WO 01/23426 A2 | 4/2001 |

OTHER PUBLICATIONS

Written Opinion of the International Searching Authority for corresponding PCT/JP2010/066893 (Japanese Mar. 31, 2012).*
English Translation of Written Opinion of the International Searching Authority for corresponding PCT/JP2010/066893 (May 8, 2012).*
Bost et al. (Immunol. Invest. 1988; 17: 577-586).*
Bendayan (J. Histochem. Cytochem. 1995; 43:881-886).*
J. Wang, et al.; "Pancreatic beta cells lack a low glucose and O2-inducible mitochondrial protein that augments cell survival;" PNAS; vol. 103; No. 28; Jul. 11, 2006; pp. 10636-10641/ Cited in International Search Report/p. 3 of specification.
N. Denko, et al.; "Epigenetic Regulation of Gene Expression in Cervical Cancer Cells by the Tumor Microenvironment;" Clinical Cancer Research; vol. 6; Feb. 2000; pp. 480-487/Cited in International Search Report/p. 2 of specification.
International Search Report for International Application No. PCT/JP2010/066893 dated Dec. 7, 2010.

* cited by examiner

*Primary Examiner* — Phillip Gambel
(74) *Attorney, Agent, or Firm* — Kratz, Quintos & Hanson, LLP

(57) ABSTRACT

This invention relates to a monoclonal antibody against a human HIG-1 polypeptide, the antibody binding to at least one epitope included in the amino acid sequence at positions 1-19 of a human HIG-1 polypeptide; an antibody fragment derived from the antibody; a DNA comprising a base sequence encoding a variable region of the antibody; an expression vector comprising the DNA; a cell line producing the antibody; a reagent for detecting a human HIG-1 polypeptide comprising the antibody or the antibody fragment, and a method for detecting a human HIG-1 polypeptide using the antibody or the antibody fragment.

10 Claims, 3 Drawing Sheets

A  ISK-MMH-TK1

B  ISK-MMH-TK2

| Antibody used (treatment concentration; 0.5 μg/mL) | Immunostaining image (× 200) |
|---|---|
| Control antibody |  |
| ISK-MMH-TK1 |  |
| ISK-MMH-TK2 |  |

MONOCLONAL ANTIBODY AGAINST HUMAN HIG-1 POLYPEPTIDE

TECHNICAL FIELD

The present invention relates to a monoclonal antibody binding to at least one epitope included in the amino acid sequence at positions 1-19 of a human HIG-1 polypeptide. The present invention also relates to an antibody fragment derived from the antibody, a DNA encoding a variable region of the antibody, an expression vector comprising the DNA, a cell line producing the antibody, a reagent containing the antibody or the antibody fragment, and a method for detecting a human HIG-1 polypeptide or a test reagent using the antibody or the antibody fragment.

BACKGROUND ART

As the population ages, rates of cancers, cardiac diseases, and cerebral vascular diseases continue to increase year by year. A common symptom of these diseases is "hypoxia" accompanied by failure of blood circulation. It is thought that reliable and sensitive detection of abnormal hypoxic symptoms hidden in vivo would not only lead to early detection of these three major diseases but also contribute to early treatment and development of novel treatments.

As such an example, Patent Literature 1 discloses a method for diagnosing a patient's tumor hypoxia including detecting the level of osteopontin (OPN) in a patient's body fluid and comparing the level with a predetermined value.

Hypoxia-induced gene 1 (HIG-1) was reported in 2000 as one of the genes induced under hypoxic conditions (Non-patent Literature 1). HIG-1 is induced also by a decrease in glucose concentration. HIG-1 is considered to be localized in an inner membrane of mitochondria and to have a function of inhibiting hypoxia-induced cell death; however, the details thereof have yet to be revealed. Patent Literature 2 and 3 also disclose the base sequences of hypoxia-induced genes HIG-1 and HIG-2, and the encoding polypeptide sequences.

Regarding a method for analyzing a HIG-1 molecule using an antibody, there has been no example of using a monoclonal antibody, and there is only a report indicating that analysis was performed using a rabbit antiserum in 2006 (Non-patent Literature 2). However, since it is difficult to stably supply a certain grade of antibody with such a polyclonal antibody, and nonspecific antibodies are included in a large amount, a detailed analysis at a molecular level is limited.

Further, neither Patent Literature 2 nor 3 discloses an example in which a monoclonal antibody against a human HIG-1 polypeptide is actually obtained.

Therefore, to solve the above problem, a monoclonal antibody that has a high affinity for a human HIG-1 polypeptide and is specifically reacted with the human HIG-1 polypeptide is desired.

CITATION LIST

Patent Literature
PTL 1: U.S. patent publication No. 2003/0044862
PTL 2: WO99/48916
PTL 3: WO01/23426
Non-patent Literature
NPL 1: Denko, N., Schindler, C., Koong, A., Laderoute, K., Green, C., and Giaccia, A., Clinical Cancer Research, Vol. 6, p. 480-p. 487, 2000.
NPL 2: Wang, J., Cao, Y., Chen, Y., Chen, Y., Gardner, P., and Steiner, D. F., Proceedings of the National Academy of Sciences, Vol. 103, p. 10636-p. 10641, 2006.

SUMMARY OF INVENTION

Technical Problem

An object of the present invention is to provide a monoclonal antibody having a high affinity for a human HIG-1 polypeptide. Another object of the present invention is to provide an antibody fragment derived from the antibody, a DNA encoding a variable region of the antibody, an expression vector comprising the DNA, a cell line producing the antibody, a reagent or test reagent containing the antibody or the antibody fragment, a method for detecting a human HIG-1 polypeptide using the antibody or the antibody fragment, etc.

Solution to Problem

The present inventors found that by producing hybridomas of myeloma cells and lymphoid cells of an animal in which a peptide fragment containing an antigen epitope of a human HIG-1 polypeptide is immunized, a high-affinity monoclonal antibody binding to a human HIG-1 polypeptide can be produced. The present invention was accomplished based on this finding and provides the following monoclonal antibody, etc.

1. A monoclonal antibody against a human HIG-1 polypeptide, the antibody binding to at least one epitope included in an amino acid sequence at positions of 1-19 of the human HIG-1 polypeptide.
2. The antibody according to Item 1, which is a mouse monoclonal antibody.
3. The antibody according to Item 1 or 2, which binds to a polypeptide obtained by expression in a cell transformed by an expression vector containing a full-length human HIG-1 gene.
4. The antibody according to Item 3, wherein the cell is an *E. coli* or human cell.
5. The antibody according to any one of Items 1 to 4, wherein the dissociation constant (Kd) of the antibody to a full-length human HIG-1 polypeptide is $9 \times 10^{-10}$ M or less.
6. The antibody according to any one of Items 1 to 5, wherein an Fc region is derived from a human.
7. The antibody according to any one of Items 1 to 5, wherein a constant region is derived from a human.
8. The antibody according to any one of Items 1 to 5, wherein a region other than a complementary determining region (CDR) is derived from a human.
9. The antibody according to any one of Items 1 to 8, wherein a heavy-chain variable region and a light-chain variable region have the following CDR:
Heavy-chain CDR 1 consisting of the amino acid sequence of SEQ ID No. 1;
Heavy-chain CDR 2 consisting of the amino acid sequence of SEQ ID No. 2;
Heavy-chain CDR 3 consisting of the amino acid sequence of SEQ ID No. 3;
Light-chain CDR 1 consisting of the amino acid sequence of SEQ ID No. 4;
Light-chain CDR 2 consisting of the amino acid sequence of SEQ ID No. 5; and
Light-chain CDR 3 consisting of the amino acid sequence of SEQ ID No. 6.
10. The antibody according to any one of Items 1 to 8, wherein a heavy-chain variable region and a light-chain variable region have the following CDR:

Heavy-chain CDR 1 consisting of the amino acid sequence of SEQ ID No. 7;
Heavy-chain CDR 2 consisting of the amino acid sequence of SEQ ID No. 8;
Heavy-chain CDR 3 consisting of the amino acid sequence of SEQ ID No. 9;
Light-chain CDR 1 consisting of the amino acid sequence of SEQ ID No. 10;
Light-chain CDR 2 consisting of the amino acid sequence of SEQ ID No. 11; and
Light-chain CDR 3 consisting of the amino acid sequence of SEQ ID No. 12.

11. An antibody fragment derived from the antibody according to any one of Items 1 to 10.

12. The antibody fragment according to Item 11, which is an Fab, Fab', F(ab')$_2$, Fv, or scFv fragment, or a single-chain antibody.

13. The antibody according to any one of Items 1 to 10, which is labeled.

14. The antibody according to Item 13, wherein the labeling is performed by an enzyme, fluorescent material, radioactive compound, or biotin.

15. The antibody fragment according to Item 11 or 12, which is labeled.

16. The antibody fragment according to Item 15, wherein the labeling is performed by an enzyme, fluorescent material, radioactive compound, or biotin.

17. The antibody according to any one of Items 1 to 10, which is tagged.

18. The antibody according to Item 17, wherein the tagging is performed by Flag, Myc, HA, GST, or histidine.

19. The antibody fragment according to Item 11 or 12, which is tagged.

20. The antibody fragment according to Item 19, wherein the tagging is performed by Flag, Myc, HA, GST, or histidine.

21. A DNA comprising a base sequence encoding a light-chain variable region or a heavy-chain variable region of the antibody according to Item 9 or 10.

22. An expression vector comprising the DNA according to Item 21.

23. A transformant transformed by the expression vector according to Item 22.

24. A DNA comprising a base sequence encoding the antibody according to Item 17 or 18.

25. An expression vector comprising the DNA according to Item 24.

26. A DNA comprising a base sequence encoding the antibody fragment according to Item 19 or 20.

27. An expression vector comprising the DNA according to Item 26.

28. A transformant transformed by the expression vector according to Item 25 or 27.

29. A cell line producing the monoclonal antibody according to any one of Items 1 to 10.

30. A hybridoma having accession number FERM BP-11266 or FERM BP-11267.

31. A reagent for detecting a human HIG-1 polypeptide comprising the antibody or antibody fragment according to any one of Items 1 to 20.

32. The reagent according to Item 31 for use in enzyme immunoassay.

33. The reagent according to Item 31 for use in Western blotting.

34. The reagent according to Item 31 for use in immunohistochemical staining.

35. The reagent according to Item 31 for use in cellular hypoxic condition evaluation.

36. The reagent according to Item 31 for use in cellular hypoglycemic condition evaluation.

37. The reagent according to Item 31 for use in cellular ischemic condition evaluation.

38. A measurement kit comprising the reagent according to any one of Items 31 to 37.

39. A method for detecting human HIG-1 using the antibody or antibody fragment according to any one of Items 1 to 20.

40. A test reagent to examine hypoxic, hypoglycemic, or ischemic conditions, comprising the antibody or antibody fragment according to any one of Items 1 to 20.

Advantageous Effects of Invention

According to the present invention, a monoclonal antibody binding to at least one epitope included in the amino acid sequence at positions 1-19 of a human HIG-1 polypeptide can be provided. By the monoclonal antibody of the present invention, a human HIG-1 polypeptide can be detected with high sensitivity, analyzed, and quantified. Therefore, the hypoxic, hypoglycemic, or ischemic conditions can be diagnosed by using the monoclonal antibody of the present invention.

BRIEF DESCRIPTION OF DRAWINGS

FIG. 1A shows the results of hybridoma ISK-MMH-TK1, and FIG. 1B shows the results of hybridoma ISK-MMH-TK2.

DESCRIPTION OF EMBODIMENTS

Figure 1:
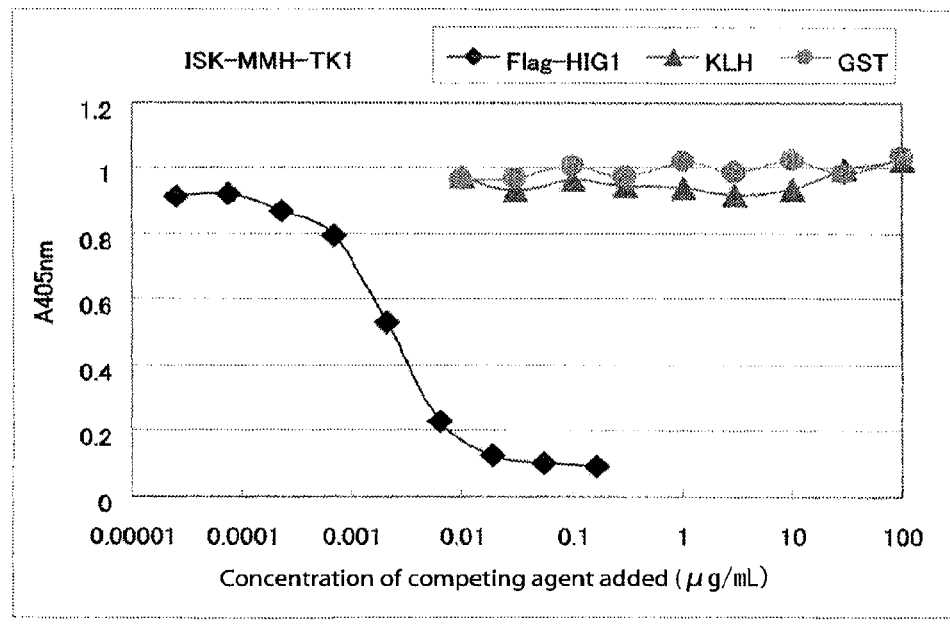
FIG. 1 shows graphs demonstrating the results of ELISA competitive reaction test using the monoclonal antibody obtained in Example 1.
Figure 1:
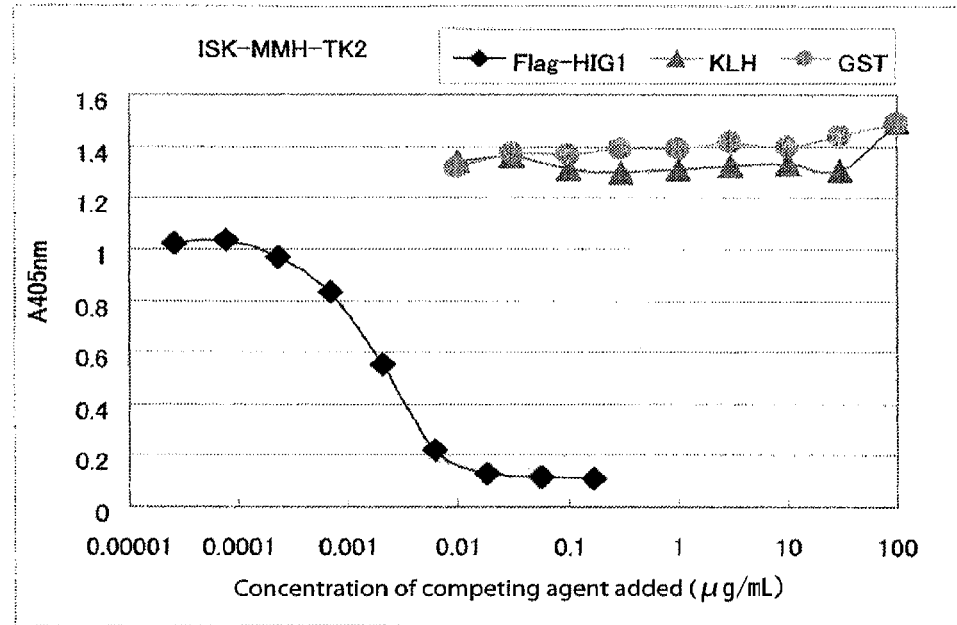

The monoclonal antibody, etc., of the present invention is explained in detail below.

Monoclonal Antibody

One of the features of the present invention is that the monoclonal antibody is a monoclonal antibody against a human HIG-1 polypeptide and binds to at least one epitope included in the amino acid sequence at positions 1-19 of the human HIG-1 polypeptide.

The class of the monoclonal antibody of the present invention is not particularly limited, and antibodies belonging to the IgG class are preferable. For example, antibodies belonging to the mouse antibody IgG1, IgG2a, IgG2b, or IgG3 are preferable.

Human HIG-1 (hypoxia-induced gene 1) is a gene induced by hypoxic conditions or a decrease in glucose concentration. A human HIG-1 polypeptide is considered to be localized mainly in the inner membrane of mitochondria. Non-patent Literature 1, and Patent Literature 2 and 3 disclose base sequences of human HIG-1 and encoding polypeptide sequences (SEQ. ID NO: 28).

The monoclonal antibody of the present invention can be derived from mice, rats, cows, rabbits, goats, sheep, guinea pigs, etc. Of these, mouse monoclonal antibodies are preferable.

One of the features of the present invention is that the antibody preferably binds to a polypeptide obtained by expression in a cell transformed by an expression vector containing a full-length human HIG-1 gene. As the cell, *E.*

*coli*, yeast, insect cells, animal cells (e.g., human cells and mouse cells), etc., can be used. Of these, *E. coli* and human cells are preferable. The monoclonal antibody of the present invention is reacted with not only a partial peptide used for immunization in producing the antibody, but also a human HIG-1 polypeptide even in a state in which the polypeptide is physiologically expressed.

The dissociation constant (Kd) of the monoclonal antibody of the present invention to the full-length human HIG-1 polypeptide is preferably $9 \times 10^{-10}$ M or less, and more preferably $3 \times 10^{-10}$ M or less. The dissociation constant can be measured by competitive ELISA, surface plasmon resonance, etc.

The monoclonal antibody of the present invention is preferably a humanized antibody, and a humanized antibody is an antibody having a similar structure to a human antibody. Examples of the humanized antibody include antibodies in which the Fc region is derived from human, antibodies in which the constant region is derived from human, antibodies in which regions other than the complementarity determining region are derived from human, etc. These humanized antibodies can be produced by a known method (e.g., method described in U.S. Pat. No. 4,816,567, Nature, Vol. 321 p. 522-p. 525, 1986).

The monoclonal antibody of the present invention preferably includes the amino acid sequences represented by SEQ ID Nos. 1 to 3 as amino acid sequences of a heavy-chain variable region and the amino acid sequences represented by SEQ ID Nos. 4 to 6 as amino acid sequences of a light-chain variable region. Further, the monoclonal antibody of the present invention preferably includes the amino acid sequences represented by SEQ ID Nos. 7 to 9 as amino acid sequences of a heavy-chain variable region and the amino acid sequences represented by SEQ ID Nos. 10 to 12 as an amino acid sequence of a light-chain variable region.

More preferably, in the monoclonal antibody of the present invention, the heavy-chain variable region and the light-chain variable region include heavy-chain CDR 1 consisting of the amino acid sequence of SEQ ID No. 1, heavy-chain CDR 2 consisting of the amino acid sequence of SEQ ID No. 2, heavy-chain CDR 3 consisting of the amino acid sequence of SEQ ID No. 3, light-chain CDR 1 consisting of the amino acid sequence of SEQ ID No. 4, light-chain CDR 2 consisting of the amino acid sequence of SEQ ID No. 5, and light-chain CDR 3 consisting of the amino acid sequence of SEQ ID No. 6. Even more preferably, in the monoclonal antibody of the present invention, the heavy-chain variable region and the light-chain variable region include heavy-chain CDR 1 consisting of the amino acid sequence of SEQ ID No. 7, heavy-chain CDR 2 consisting of the amino acid sequence of SEQ ID No. 8, heavy-chain CDR 3 consisting of the amino acid sequence of SEQ ID No. 9, light-chain CDR 1 consisting of the amino acid sequence of SEQ ID No. 10, light-chain CDR 2 consisting of the amino acid sequence of SEQ ID No. 11, and light-chain CDR 3 consisting of the amino acid sequence of SEQ ID No. 12.

The sequence of the framework region (FR region) in the variable region of the monoclonal antibody of the present invention is not particularly limited as long as the binding ability to at least one epitope included in the amino acid sequence at positions 1-19 of the human HIG-1 polypeptide is not adversely affected.

The antibody fragment of the present invention can be produced from the antibody of the present invention or on the basis of the sequence information of the gene encoding the antibody. Examples of the antibody fragment include Fab, Fab', F(ab')$_2$, Fv, scFv, and the like.

Fab is a fragment with a molecular weight of about 50,000 that consists of L-chain and H-chain fragments. Fab is obtained by digesting IgG with papain in the presence of cysteine. The Fab of the present invention can be obtained by digesting the monoclonal antibody with papain. Alternatively, Fab can be produced by a transformant obtained by transformation using a vector into which a DNA encoding the Fab is introduced.

Fab' is a fragment with a molecular weight of about 50,000 obtained by cleaving the disulfide bond between the H chains of F(ab')$_2$ described below. The Fab' of the present invention can be obtained by digesting the monoclonal antibody with pepsin and cleaving the disulfide bond using a reducing agent. Alternatively, Fab' can be produced by a transformant obtained by transformation using a vector into which a DNA encoding the Fab' is introduced.

F(ab')$_2$ is a fragment with a molecular weight of about 100,000 obtained by digesting IgG with pepsin. F(ab')$_2$ is constituted by Fab' fragments linked together via a disulfide bond, each of which consists of L-chain and H-chain fragments. The F(ab')$_2$ of the present invention can be obtained by digesting the monoclonal antibody with pepsin. Alternatively, F(ab')$_2$ can be produced by a transformant obtained by transformation using a vector into which a DNA encoding the F(ab')$_2$ is introduced.

Fv is an antibody fragment consisting of H-chain and L-chain variable regions. The Fv of the present invention can be produced by a transformant obtained by transformation using a vector into which a DNA encoding the H chain and the L-chain variable regions of the monoclonal antibody is introduced.

scFv is an antibody fragment in which Fv consisting of H-chain and L-chain variable regions is linked via an appropriate peptide linker. The scFv of the present invention can be produced by a transformant obtained by transformation of a vector for scFv expression, which is produced by a DNA encoding the H-chain variable region and the L-chain variable region of the monoclonal antibody.

The monoclonal antibody and the antibody fragment of the present invention may be labeled with an enzyme, fluorescent material, radioactive compound, biotin, etc. Examples of the enzyme include peroxidase, β-D-galactosidase, micro peroxidase, horseradish peroxidase (HRP), alkaline phosphatase, and the like. Examples of the fluorescent material include fluorescein isothiocyanate (FITC), phycoerythrin (PE), and the like. Examples of the radioactive compound include $^{125}$I, $^{131}$I, and the like.

The monoclonal antibody and the antibody fragment of the present invention may be tagged. Examples of the tag include Flag, Myc, HA (hemagglutinin), GST (glutathione-S-transferase), histidine, etc. A DNA encoding a tag is added to a DNA encoding the antibody or antibody fragment of the present invention, and the DNA is introduced into a vector. The tagged antibody or antibody fragment is produced by a transformant obtained by transformation using the vector.

The monoclonal antibody of the present invention can be produced by a hybridoma obtained by immunizing a peptide having an amino acid sequence at positions 1-19 of a human HIG-1 polypeptide in an animal.

Since the molecular weight of the peptide is so small that it cannot induce immune response as is, the peptide is conjugated with an appropriate protein and used as an immunogen. Preferable examples of the conjugate used include bovine serum albumin, ovalbumin, keyhole limpet hemocyanin (KLH), etc. In particular, keyhole limpet hemocyanin (KLH)

is preferable. To enhance immunoreaction, the above immunogen can be mixed with an appropriate adjuvant before immunization reaction.

Examples of animals used for immunization include mammals such as mice, rats, cows, rabbits, goats, sheep, and guinea pigs, and mice are particularly preferable.

The monoclonal antibody of the present invention can be obtained as follows. For example, a mixture in which KLH is conjugated with a peptide having an amino acid sequence at positions 1-19 of a human HIG-1 polypeptide is used as an immunogen to produce hybridomas, and then hybridomas that produce antibodies reacted with the aforementioned peptide are selected and subjected to cloning. The thus produced monoclonal antibody is purified. Immunization can be generally performed using 1 ng to 10 mg of an immunogen in 1 to 5 separate times with intervals of 10 to 14 days. After sufficient immunization, an organ (spleen or lymph node) in which antibody-producing cells are accumulated is aseptically excised from an animal and is used as a parent cell in cell fusion. As the excised organ, a spleen or lymph node is preferable. As a cell fusion partner, a myeloma cell can be used. The myeloma cell is derived from a mouse, rat, human, etc., and the myeloma cell derived from a mouse is preferable. The cell fusion can be performed by a method using an inactivated Sendai virus, a method using polyethylene glycol, a cell electrofusion method, or the like. A method using an inactivated Sendai virus is preferable because it is simple, and high fusion efficiency can be obtained. The selection of hybridomas from spleen cells or myeloma cells, which do not undergo cell fusion, can be performed by culturing them in a serum medium in which a HAT supplement (hypoxanthine aminopterin thymidine) is added.

A hybridoma producing an antibody against a human HIG-1 polypeptide is preferably selected by extracting the aforementioned culture supernatant and performing ELISA in a plate in which a peptide having an amino acid sequence at positions 1-19 of the human HIG-1 polypeptide is immobilized. As a result of ELISA, wells in which strong coloring is observed are selected, and cells in the wells are subjected to cloning. The process (cloning) of selecting and unifying an antibody-producing hybridoma can be performed by a limiting dilution method, a fibrin gel method, a method using a cell sorter, or the like, and the limiting dilution method is preferable because it is simple. Thereby, a hybridoma producing the target monoclonal antibody can be obtained.

By culturing the hybridoma obtained by the aforementioned method, a monoclonal antibody can be obtained in a culture supernatant. To obtain a large amount of the monoclonal antibody, in vivo or in vitro methods are known, and the method can be selected according to the purpose. The monoclonal antibody can be purified from a culture supernatant or mouse ascites by ammonium sulfate precipitation, affinity chromatography, ion-exchange chromatography, hydroxyapatite column chromatography, or the like. From the viewpoint of refining purity and easiness, affinity chromatography is most preferable. Further, when the monoclonal antibody having a high purity is required, it is preferable to perform gel filtration chromatography, ion exchange chromatography, etc., as the final refining after affinity chromatography.

Cell Line

One feature of the present invention is that the cell line produces the aforementioned monoclonal antibody.

Examples of the cell line include hybridomas produced by the aforementioned method. In particular, hybridomas of mouse spleen cells and inbred mouse myeloma cells are preferable.

The cell line of the present invention is preferably hybridomas of accession number FERM BP-11266 or FERM BP-11267.

DNA Comprising a Base Sequence Encoding a Variable Region of Antibody

One feature of the present invention is that a DNA comprising a base sequence encoding light-chain or heavy-chain variable regions of the monoclonal antibody.

Specific examples thereof include a DNA encoding a heavy-chain variable region having heavy-chain CDR 1 consisting of the amino acid sequence of SEQ ID No. 1, heavy-chain CDR 2 consisting of the amino acid sequence of SEQ ID No. 2, and heavy-chain CDR 3 consisting of the amino acid sequence of SEQ ID No. 3; a DNA encoding a light-chain variable region having light-chain CDR 1 consisting of the amino acid sequence of SEQ ID No. 4, light-chain CDR 2 consisting of the amino acid sequence of SEQ ID No. 5, and light-chain CDR 3 consisting of the amino acid sequence of SEQ ID No. 6; a DNA encoding a heavy-chain variable region having heavy-chain CDR 1 consisting of the amino acid sequence of SEQ ID No. 7, heavy-chain CDR 2 consisting of the amino acid sequence of SEQ ID No. 8, and heavy-chain CDR 3 consisting of the amino acid sequence of SEQ ID No. 9; and a DNA encoding a light-chain variable region having light-chain CDR 1 consisting of the amino acid sequence of SEQ ID No. 10, light-chain CDR 2 consisting of the amino acid sequence of SEQ ID No. 11, and light-chain CDR 3 consisting of the amino acid sequence of SEQ ID No. 12.

The DNA of the present invention can be produced by known methods, such as chemical synthesis and biochemical breakage/reunion. The DNA can be used for producing an antibody or antibody fragment that binds to at least one epitope included in the amino acid sequence at positions 1 to 19 of a human HIG-1 polypeptide.

One of the features of the present invention is that the expression vector comprises the aforementioned DNA. Using the expression vector of the present invention, a host cell can be transformed. The kind of the vector used is not particularly limited as long as the DNA of the present invention can be expressively incorporated and expressed in a host cell. The host cell is not particularly limited as long as it is transformed by the expression vector of the present invention, and it can express the DNA of the present invention. Examples thereof include animal cells such as COS cells and CHO cells.

Reagent for Detecting Human HIG-1 Polypeptide

The reagent of the present invention is a reagent for detecting a human HIG-1 polypeptide, and one of the features is that the reagent contains the aforementioned monoclonal antibody or the antibody fragment.

Purposes of the reagent include enzyme-linked immunosorbent assay (ELISA), Western blotting, immunohistochemical staining, evaluation of hypoxic conditions of cells, evaluation of hypoglycemic conditions of cells, evaluation of ischemic conditions of cells, and the like.

ELISA can be performed according to a general comparative method, sandwich method, or the like.

For example, ELISA can be performed as follows. A standard antigen (human HIG-1 polypeptide) is immobilized to a suitable carrier, and blocking is performed. Subsequently, a sample containing a human HIG-1 polypeptide and the antibody of the present invention are brought into contact with the immobilized standard antigen to competitively form the antibody of the present invention-human HIG-1 polypeptide in the sample immuno complex and the antibody of the present invention-standard antigen immuno complex. The amount of the obtained antibody of the present invention-standard antigen immuno complex is measured. The amount of the human HIG-1 polypeptide in the sample can be determined from the calibration curve produced beforehand.

In ELISA, it is also possible to use the antibody of the present invention as the primary antibody and use the secondary antibody against the primary antibody after labeling. In this case, the amount of the antibody of the present invention-human HIG-1 polypeptide immuno complex can be easily obtained by measuring the labeled amount of the labeled secondary antibody bonded thereto. As a modified method of the aforementioned method, it is also possible to label the primary antibody with for example, enzyme, without using the labeled secondary antibody.

Western blotting can be performed, for example, as follows. After a sample solution is subjected to acrylamide gel electrophoresis, the solution is transferred to a membrane and reacted with the antibody of the present invention. The thus formed reaction mixture (immuno complex) is detected using a labeled secondary antibody.

One of the features of the measurement kit of the present invention is that the kit comprises the aforementioned reagent. The measurement kit preferably includes a required amount of a reagent necessary for the measurement method used, in addition to the reagent. Such a kit is used, for example, for detecting a human HIG-1 polypeptide using ELISA, in which the monoclonal antibody or antibody fragment of the present invention is used as an antibody for solid phase adsorption, and/or a labeled antibody for detection, and the labeled antibody for detection is labeled by HRP. The kit includes other reagents (for example, microplate, extracted solution, buffer solution, etc.) necessary for ELISA.

Method for Detecting Human HIG-1 Polypeptide

The method of the present invention is a method for detecting a human HIG-1 polypeptide, and has a feature of using the aforementioned monoclonal antibody or the antibody fragment.

The method can be performed according to an ordinary method such as Western blotting, immunoblot, enzyme-linked immunosorbent assay (ELISA), radioimmunoassay (RIA), chemiluminescent immunoassay (CLIA), fluorescent immunoassay (FIA), latex agglutination assay (LA), turbidimetric immunoassay (TIA), and immuno chromatography. In the method of the present invention, ELISA and western blotting are preferable. The method is preferably performed in vitro.

According to the method of the present invention, a human HIG-1 polypeptide can be detected with high accuracy and high sensitivity. This detection results are useful in evaluation under hypoxic conditions, hypoglycemic conditions, or ischemic conditions. By the results, it is possible to obtain an index effective for the early detection of cancers, cardiac diseases, and cerebral vascular diseases.

Test Reagent

The test reagent of the present invention is a test reagent of hypoxic conditions, hypoglycemic conditions, or ischemic conditions, and has a feature in that it includes the aforementioned monoclonal antibody or the antibody fragment.

By quantitatively or qualitatively measuring a human HIG-1 polypeptide using a detection method such as Western blotting, immunoblot, enzyme-linked immunosorbent assay (ELISA), radioimmunoassay (RIA), chemiluminescent immunoassay (CLIA), fluorescent immunoassay (FIA), latex agglutination assay (LA), turbidimetric immunoassay (TIA), or immuno chromatography, the hypoxic conditions, hypoglycemic conditions, or ischemic conditions can be examined by the test reagent. The test reagent of the present invention is preferably used as an in vitro test reagent. Further, the present invention also provides a detection kit including the test reagent.

The monoclonal antibody or the antibody fragment of the present invention is expected to be used in the treatment of cancers, etc.

EXAMPLES

Hereinafter, the present invention is explained in detail with reference to the Examples. However, the technical scope of the present invention is not limited to these Examples.

Example 1

Preparation of Monoclonal Antibody (1) Preparation of Antigen
1-1) Synthesis of Human HIG-1 Partial Peptide (20 Amino Acids)

The synthesis of partial peptide CMSTDTGVSLPSY-EEDQGSK (SEQ ID No. 13) (20 amino acids) (hereinafter abbreviated as HIG-1p20) in which cysteine for forming a carrier protein complex was added to the N terminal of the amino acid sequence at positions 1 to 19 of a human HIG-1 polypeptide was assigned to Toray Research Center, Inc. (Tokyo) to make peptide (purity: 98%).

1-2) Production of Hapten-Carrier Protein Complex

Using a kit for producing a hapten-carrier protein complex (Pierce Biotechnology, Inc., No. 77607, MBS method), a complex of HIG-1p20 and carrier protein was produced. That is, 0.2 mL of a 10 mg/mL maleimide activated carrier protein and 0.2 mL of a 1 mg/mL HIG-1p20 synthetic peptide were mixed, and the mixture was allowed to stand at room temperature for 2 hours for the reaction. Thereafter, dialysis was performed using 10 mM phosphate buffer physiological saline at pH 7.4 (PBS) at 4° C. for 24 hours. As a carrier protein, keyhole limpet hemocyanin (KLH) or bovine serum albumin (BSA) was used.

(2) Animal Immunization 2 mg/mL of an antigen (HIG-1p20-KLH) was mixed with an equivalent amount of Freund's Complete Adjuvant (CFA) (Sigma, F-5881) to produce an emulsion, and the emulsion was intradermally injected into the base of the tail of each BALb/c mouse (female, 6 to 8 weeks old) in an amount of 0.1 mL (antigen 0.1 mg) per mouse. Two weeks later, mice were intraperitoneally boosted with a mixture of 0.1 mg/mL of antigen and an equivalent amount of Alum adjuvant (Pierce, 77140) in an amount of 0.2 ml (antigen 0.01 mg) per mouse. At intervals of one week to two weeks from the initial immunization, blood was collected from the tail vein, and the antibody titer was checked.

(3) Measurement of Antibody Titer

The antibody titer was measured by enzyme-linked immunosorbent assay (ELISA). Specifically, as an antigen, HIG-1p20-BSA was coated at a concentration of 10 µg/mL (50 mM carbonate buffer solution, pH 9.6, Sigma, No. C3041) in an amount of 50 µL per well, onto a 96-well plate (IWAKI, Co., Ltd. No. 3801-096) at room temperature. Washing was performed 3 times with PBS (PBS-T) containing 0.05 w/v % Tween® 20, (polyethylene sorbitol ester), and then blocking was conducted for 1 hour with PBS containing 10 v/v % fetal bovine serum (10% FBS). After the blocking agent was removed by inhalation, mouse serum subjected to stepwise dilution (200-fold, 2,000-fold, or 20,000-fold) using PBS-T (10% FBS-PBS-T) containing 10% FBS was placed in an amount of 50 µL per well and allowed to stand at room temperature for 1 hour.

After washing was performed with PBS-T 3 times, an alkaline phosphatase-labeled secondary antibody (anti-mouse IgG, Sigma, No. A3563) diluted 1,000-fold with 10% FBS-PBS-T was placed in an amount of 50 µL per well, and the mixture was allowed to stand for 1 hour. Washing was then performed with PBS-T 5 times, and a 0.1 M glycine buffer solution (pH 10.4) containing 1 mg/mL of p-nitrophenylphosphate (Sigma, No. N9389) was placed in an amount of 100 µL per well. The mixture was allowed to stand for 20 minutes at 37° C. After the reaction, the absorbance of 405 nm was measured (SPECTRAmax® 250, microplate reader produced by Molecular Devices, LLC). As a result, an increase in the antibody titer against the antigen was confirmed even in the 20,000-fold diluted serum solution.

Cell fusion was performed using a Sendai virus envelope (Hemagglutinating virus of Japan envelope; HVJ-E) method (GenomONE™-CF cell fusion kit No. CF004, produced by Ishihara Sangyo Kaisha, Ltd.) in a ratio such that myeloma cells X-63-Ag 8.653 and the spleen cells of a mouse in which the antibody titer increase was confirmed was 1:5, and the hybridoma was subjected to selective culturing in a 10% FBS-containing RPMI-1640 medium (Sigma, No. R8785) containing HAT (Gibco, No. 21060-017) and HT (Gibco, No. 11067-030). The hybridoma culture supernatant was collected on day 10 to 12 of cell fusion, and screening was performed by ELISA according to the same method as in the measurement of the antibody titer (see Item (3) above).

The number of hybridoma cells selected in the screening was calculated, and the cells were seeded onto a 96-well plate in a manner such that each well contained 0.5 cells, followed by cloning by a limiting dilution method. Similarly, a hybridoma that became positive in the ELISA screening was again subjected to subcloning to select ISK-MMH-TK1 and ISK-MMH-TK2. The results of isotyping (Mouse Monoclonal Antibody Isotyping Test kit, DS Pharma Biomedical, No. MMT1) of these antibodies in a culture supernatant indicate that they were IgG1κ and IgG3κ, respectively.

The obtained hybridomas, ISK-MMH-TK1 and ISK-MMH-TK2, were deposited with the National Institute of Advanced Industrial Science and Technology International Patent Organism Depositary, (Tsukuba Central 6, 1-1-1 Higashi, Tsukuba-shi, Ibaraki-ken, Japan) on Aug. 18, 2009, under accession Nos. FERM P-21835 and FERM P-21836, respectively, and internationally deposited under accession Nos. FERM BP-11267 and FERM BP-11266, respectively.

Example 2

Preparation of HIG-1-Flag Protein (1) Production of Transformant

In this example, HIG-1 represents human HIG-1, unless otherwise specified.

10 µL of an *E. coli* competent cell (Rosetta® (DE3), Novagen No. 709543) and 1 µL of glutathione S transferase (GST)-HIG-1-Flag expression plasmid pGST-HIG-1-Flag (plasmid in which HIG-1 was inserted into a multiple cloning site of pGEX 6P-1 (GE Healthcare) and a flag tag sequence was inserted into the downstream of the HIG-1) were mixed, incubated on ice for 30 minutes, subjected to a heat shock treatment for 30 seconds at 42° C., and incubated on ice for 2 minutes. Thereafter, the mixture was diluted in 100 µL SOC medium (Novagen No. 709543, accessories), and cultured by shaking at 37° C. for 1 hour. The mixture was then applied onto a LB plate (20 µg/mL kanamycin, 34 µg/mL chloramphenicol, 10 mg/mL peptone, 5 mg/mL yeast extract, 10 mg/mL sodium chloride, pH 7.4) to produce a recombinant colony.

(2) Cultivation and Harvest

A colony generated in the plate was added to 100 mL of LB medium, and culturing was performed in a flask at 37° C. and 300 rpm overnight. The total amount of the culture solution was mixed with 1.5 L of a LB medium, and culturing was performed at 37° C. and 150 rpm until $OD_{600}$=0.6. After the resultant was allowed to stand at 15° C. for 30 minutes, isopropyl-β-thio galactopyranoside (IPTG) (Nacalai Tesque, Inc.) was added thereto to bring the final concentration to 0.5 mM, and the mixture was cultured by shaking in a flask at 15° C. for about 16 hours. The wet weight of the centrifuged cell was measured, and the cell was suspended in a sonication buffer (50 mM Tris-HCl (pH 8.0), 0.15 M NaCl, 1 mM EDTA) in an amount of 5 mL per gram of a wet cell. After sonication under ice cooling (15 seconds, interval of 30 seconds×5), Triton™-100 (nonionic surfactant) was added so that the concentration became 0.2 w/v %, and mixing by inversion was performed at 4° C. for 30 minutes. The cell homogenate was centrifuged at 4° C., 10,000 g, for 30 minutes, and then the centrifugal supernatant was passed through a 0.45 µm filter. Since a PreScission Protease recognition sequence is present between the GST and HIG-1-Flag of a GST-HIG-1-Flag, GST was cleaved according to the following process to prepare a HIG-1-Flag. Specifically, the filter-passed cell homogenate, a PreScission Protease reaction solution (50 mM Tris-HCl (pH 7.5), 0.15 M NaCl, 1 mM EDTA, 1 mM DTT), and a PreScission Protease (GE Healthcare, No. 27-0843-01) solution were sequentially passed into a GST column (GSTrap FF produced by GE Healthcare, No. 17-5130-01), and the column was allowed to stand at 4° C. overnight. After GST was cleaved, a PreScission Protease reaction solution was added to the GST column to collect a HIG-1-Flag solution. This solution was substituted with PBS by using a dialysis membrane (Spectra/Por6 MWCO: 1000, Spectrum Laboratories, Inc., No. 132636) to thereby obtain a HIG-1-Flag solution.

Example 3

Examination 1 of the Properties of the Monoclonal Antibody of the Present Invention In this example, the specific properties of the monoclonal antibody to a HIG-1 polypeptide were confirmed by an ELISA competitive reaction test.

Specifically, the HIG-1-Flag obtained in Example 2 as a solid-phase antigen was coated at a concentration of 2.5 µg/mL (50 mM carbonate buffer solution, pH 9.6, Sigma, No. C3041) in an amount of 50 µL per well, onto a plate at room temperature for 1 hour. Washing was performed 3 times with PBS-T, and then blocking was conducted with PBS (10% FBS-PBS) containing 10% FBS for 1 hour. After washing was performed 3 times with PBS-T, the PBS-T diluent of the antibody culture supernatant obtained in Example 1 was mixed with a diluted solution of a competitive substance (serial dilution with PBS-T) and reacted at room temperature for 1 hour. The reaction mixture was placed in a plate in an amount of 50 µL., per well and allowed to stand for 1 hour at room temperature. In the preliminary test, the dilution rate of the antibody culture supernatant was determined beforehand so that the absorbance became around 1 when there was no competitive substance (ISK-MMH-TK1 was diluted 20,000-fold and ISK-MMH-TK2 was diluted 3,200-fold.). As competitive substances, a HIG-1-Flag (on which 3-fold serial dilution was performed 8 times from 0.167 µg/mL), KLH (on which 3-fold serial dilution was performed 8 times from 100 µg/mL), or GST (on which 3-fold serial dilution was performed 8 times from 100 µg/mL) was used. After washing was performed using PBS-T 3 times, the alkaline phosphatase-labeled secondary antibody (anti-mouse IgG) diluted 1,000-fold with 10% FBS-PBS-T was placed in an amount of 50 µL per well and allowed to stand at room temperature for 1 hour. After washing was performed with PBS-T 5 times, 1 mg/mL of a 0.1M glycine buffer solution (pH 10.4) containing p-nitrophenylphosphate was placed in an amount of 100 µL per well and reacted at 37° C. for 1 hour. After reaction, the 405 nm absorbance was measured. FIG. 1 shows the results of ISK-MMH-TK1 and ISK-MMH-TK2 obtained in Example 1.

These antibodies were both capable of quantitatively measuring a HIG-1-Flag in the range of 0.7 to 6.2 ng/mL. The dissociation constant Kd of the monoclonal antibody to a HIG-1-Flag was calculated with reference to "Antibody engineering; A Practical Approach" (edited by McCafferty J., et al.), Chapter 4, 77-97, IRL Press Oxford. Consequently, the Kd of the monoclonal antibody produced by each clone was $2.2 \times 10^{-10}$ M (ISK-MMH-TK1), and $1.7 \times 10^{-10}$ M (ISK-MMH-TK2).

Example 4

Examination 2 of the Properties of the Monoclonal Antibody of the Present Invention In this example, the reactivity of the monoclonal antibody in the Western blotting was confirmed.

Figure 2:
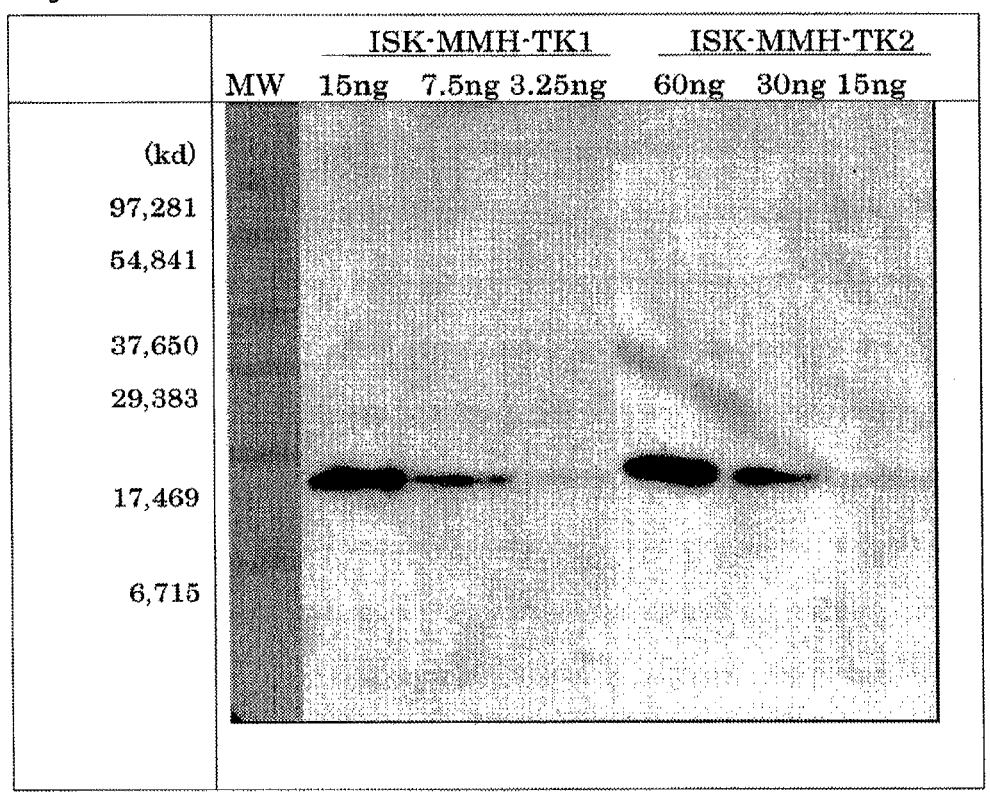
FIG. 2 shows the results of Western blotting using the monoclonal antibody obtained in Example 1.

The HIG-1 Flag produced in Example 2 was subjected to SDS-PAGE (15 w/v % gel), and then transferred to a clear blot membrane (Atto Corporation, No. AE-6667). Thereafter, blocking was performed at 4° C. for 16 to 18 hours in a 20 mM tris buffered physiological saline solution (TBS-T) containing 0.1 w/v % Tween® 20 (polyethylene sorbitol ester) including 5 w/v % skim milk (Morinaga Milk Industry Co., Ltd.). In this example, the processes hereinbelow were performed at room temperature unless otherwise specified. After the blocking agent was removed, reaction was performed for 1 hour with an antibody culture supernatant obtained in Example 1, which was adjusted to have a concentration of 0.5 µg/mL using 10% FBS-PBS-T. The membrane was washed with TBS-T 3 times and reacted with a secondary labeled antibody (Anti-Mouse IgG, HRP-Linked Whole Ab Sheep, GE Healthcare, No. NA931-100UL) diluted 5,000-fold with TBS-T for 1 hour. Subsequently, the membrane was washed with TBS-T 3 times, reacted with a luminescent substrate, ECL Plus Western Blotting Detection Reagents (GE Healthcare, No. RPN2132) for 5 minutes, and analyzed by using an LAS-3000 lumino image analyzer (Fujifilm Corporation). FIG. 2 shows the results.

As a result, the band depending on the amount of HIG-1-Flag protein was detected in the range of 3.25 ng to 15 ng in ISK-MMH-TK1 and in the range of 15 ng to 60 ng in ISK-MMH-TK2.

Example 5

Examination 3 of the Properties of the Monoclonal Antibody of the Present Invention In this example, the reactivity of the monoclonal antibody to an HIG-1 molecule in which a gene was introduced into a cell and expressed therein was confirmed.

SAS (human tongue epidermoid cancer) cells ($3 \times 10^4$ cells /well) were suspended and seeded in a 10% FBS-containing D'MEM (Sigma, No. D5796) solution in a 48-well culture plate (Corning, No. 3548), and cultured for 1 day (37° C., 5% $CO_2$). A complex of Lipofectamine® (transfection reagent) 2000 (Invitrogen, No. 11668-027) and a plasmid DNA of pCAG-Flag-HIG-1 (plasmid in which a Flag tag sequence was inserted into the downstream of the CAG promoter and a HIG-1 sequence was inserted into the downstream thereof) was added to introduce the gene, and culturing was performed for one further day. Thereafter, washing was performed using PBS 2 times, and immunity staining was performed by the following methods.

Figure 3:
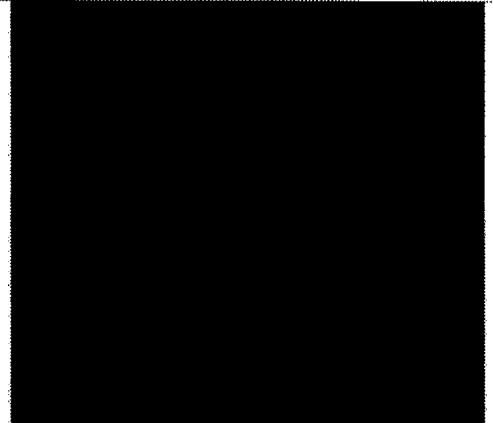
FIG. 3 shows the results of cellular immunostaining using the monoclonal antibody obtained in Example 1.
Figure 3:
Figure 3:

That is, cells were fixed using 4 w/v % paraformaldehyde (room temperature for 10 minutes), washed with PBS 1 time, and treated with PBS containing 0.2 w/v % Triton™ X-100 (nonionic surfactant) at room temperature for 5 minutes. Subsequently, washing was performed with PBS 2 times, and blocking was performed at 4° C. for 16 to 18 hours using PBS containing 1 w/v % BSA. Thereafter, reaction was performed at room temperature for 1 hour with the antibody culture supernatant obtained in Example 1, which was adjusted to have a concentration of 0.5 µg/mL by 10% FBS-PBS-T. As a negative control, a commercially available control mouse antibody (IgG1κ from murine myeloma, Sigma, No. M9269-1MG produced) was used. Subsequently, washing was performed with PBS 3 times, and reaction with an Alexa Fluor® 488 fluorescent labeled anti-mouse IgG antibody (Invitrogen No. A11017) diluted 500-fold with 10% FBS-PBS-T was performed at room temperature for 1 hour. After washing was performed 3 times with PBS, observation was conducted using a fluorescence microscope (Olympus Corporation, No. IX70). All washing processes in this example were carried out at room temperature. FIG. 3 shows the results.

Example 6

Analysis of the Variable Region of the Monoclonal Antibody of the Present Invention The gene sequences of the variable regions of ISK-MMH-TK1 and ISK-MMH-TK2 were analyzed by the following method.

Total RNAs were extracted from hybridomas ISK-MMH-TK1 and ISK-MMH-TK2, using an RNeasy Mini kit (QIAGEN). The obtained total RNAs were subjected to reverse transcription reaction using Ready-To-Go You-Prime First-Strand Beads (GE Healthcare) to synthesize cDNA. Primers used for the reverse transcription reaction were designed to match a respective L-chain or H-chain constant region. The primer sequences are as follows.

```
L chain (both ISK-MMH-TK1 and ISK-MMH-TK2):
                                        (SEQ ID No. 14)
cgactagtcgactggtgggaagatggatacag;

H chain of ISK-MMH-TK1:
                                        (SEQ ID No. 15)
cgacaagtcgactagcccttgaccaggcatcc;
and H chain of ISK-MMH-TK2:
                                        (SEQ ID No. 16)
cgactagtcgactagcctttgacaaggcatcc.
```

Using these cDNAs as templates, the following PCR reaction was performed. Specifically, PCR reaction was carried out by performing 10 cycles of a step including 94° C. for 30 seconds, 55° C. for 30 seconds, and 72° C. for 30 seconds using a GeneAmp® PCR system 9700 (Applied Biosystems), and then 20 to 25 cycles of a step including 94° C. for 30 seconds, 60° C. for 30 seconds, and 72° C. for 30 seconds. Ex Taq™ (DNA polymerase, Takara Bio Inc.) was used as a PCR enzyme. The primer set used in the PCR reaction was designed to match the leader sequence and the constant region to amplify the respective L-chain or H-chain variable region. These primer sequences are as follows.

```
L chain (both ISK-MMH-TK1 and ISK-MMH-TK2):
                                             (SEQ ID No. 17)
ctgwtgttctggattcctg
and
         (SEQ ID No. 14, also used in reverse transcription)
cgactagtcgactggtgggaagatggatacag;

H chain (ISK-MMH-TK1):
                                             (SEQ ID No. 18)
ctcctgtcaktaactkcaggt
and
         (SEQ ID No. 15, also used in reverse transcription)
cgacaagtcgactagcccttgaccaggcatcc;
and H chain (ISK-MMH-TK2):
                                             (SEQ ID No. 19)
tgttgacagycvttcckggt
and
         (SEQ ID No. 16, also used in reverse transcription)
cgactagtcgactagcctttgacaaggcatcc.
Note:
w = a or t,
k = t or g,
y = t or c,
v = a, c, or g.
```

A PCR amplified product was subjected to 2 w/v % agarose gel electrophoresis. In the case of a single band, purification was performed using a QIA quick PCR Purification Kit (QIAGEN), and in the case of a plurality of bands, a portion containing a target DNA fragment was excised from an electrophoresis gel, and purified using Wizard® SV Gel and a PCR Clean-Up System (Promega). These purified PCR amplified products were used as template DNAs in the sequence reaction. The sequence reaction was performed using a BigDye® Terminator Cycle Sequencing Kit (Applied Biosystems) and primers used in the PCR reaction, and the sequence analysis was conducted using a 3100-Avant Genetic Analyzer (Applied Biosfystems). The primer sequences used in the sequence reaction are as follows.

```
L chain (both ISK-MMH-TK1 and ISK-MMH-TK2):
                                             (SEQ ID No. 17)
ctgwtgttctggattcctg
or
                                             (SEQ ID No. 14)
cgactagtcgactggtgggaagatggatacag;

H chain (ISK-MMH-TK1):
                                             (SEQ ID No. 18)
ctcctgtcaktaactkcaggt
or
                                             (SEQ ID No. 15)
cgacaagtcgactagcccttgaccaggcatcc;
and H chain (ISK-MMH-TK2):
                                             (SEQ ID No. 19)
tgttgacagycvttcckggt
or
                                             (SEQ ID No. 16)
cgactagtcgactagcctttgacaaggcatcc.
```

As a result of the sequence analysis, the presumed sequences of DNA fragments (primer sequence regions are written in small letters) amplified by the PCR reaction, amino acid sequences translated based on the DNA sequences, and amino acid sequences of CDRs determined from the amino acid sequences are as follows. The amino acid sequence of each CDR was determined by referring to "Infection and Immunity, Vol. 68, pp. 1871-1878, 2000."

ISK-MMH-TK1 L chain (DNA sequence)
(SEQ ID No. 20)
ctgwtgttctggattcctgCTTCCAGCAGTGATGTTTTGATGACCCAAACTCCACTCTCCCTGCC

TGTCAGTCTTGGAGATCAAGCCTCCATCTCTTGCAGATCTAGTCAGAGCATTGTACATAGTAATG

GAAACACCTATTTAGAATGGTACCTGCAGAAACCAGGCCAGTCTCCAAAGCTCCTGATCTACAAA

GTTTCCAACCGATTTTCTGGGGTCCCAGACAGGTTCAGTGGCAGTGGATCAGGGACAGATTTCAC

ACTCAAGATCAGCAGAGTGGAGGCTGAGGATCTGGGAGTTTATTACTGCTTTCAAGGTTCACATG

TTCCGTGGACGTTCGGTGGAGGCACCAAGCTGGAAATCAAACGGGCTGATGCTGCACCAActgta tccatcttcccaccagtcgactagtcg ISK-MMH-TK1 H chain (DNA sequence)
(SEQ ID No. 21)
ctcctgtcaktaactkcaggtGTCCTCTCTGAGGTCCAGCTGCAACAGTCTGGACCTGAGCTGGT

GAAGCCTGGGGCTTCAGTGAAGATTTCCTGCAAGACTTCTGGATACACATTCACTAAATACACCA

TGCACTGGGTGAAGCAGAGCCATGGAAAGAGCCTTGAGTGGATTGGAGGTATTAATCCTAACAAT

GGTGGTAGTAGGTATGACCAGAAGTTCAGGGGCAAGGCCACATTGACTGTAGACAAGTCCTCCAG

CACAGCCTACATGGAGTTCCGCAGCCTGACATCTGAGGATTCTGCAGTCTATTACTGTGCAAGAG

ACTTTGTTTACTGGGGCCAAGGGACTCTGGTCACTGTCTCTGCAGCCAAAACGACACCCCCATCT

GTCTATCCACTGGCCCCTGGATCTGCTGCCCAAACTAACTCCATGGTGACCCTGggatgcctggt caagggctagtcgacttgtcg ISK-MMH-TK2 L chain (DNA sequence)
(SEQ ID No. 22)
ctgwtgttctggattcctgCTTCCAGCAGTGATGTTGTGATGACCCAAATTCCACTCTCCCTGCC

TGTCAGTCTTGGAGATCAAGCCTCCATCTCTTGCAGATCTACTCAGAGCCTTGTACACAGTAATG

GAAACACCTATTTACATTGGTTCCTGCAGAAGCCAGGCCAGTCTCCAAAGCTCCTGATCTACAAA

GTTTCCAACCGATTTTCTGGGGTCCCAGACAGGTTCAGTGGCAGTGGATCAGGGACAGATTTCAC

ACTCAAGATCAGCCGAGTGGAGGCTGAGGATCTGGGAGTTTATTTCTGCTCTCAAAGTAAATATG

TTCCTCGGACGTTCGGTGGAGGCACCAAGCTGGAAATCAAACGGGCTGATGCTGCACCAActgta tccatcttcccaccagtcgactagtcg ISK-MMH-TK2 H chain (DNA sequence)
(SEQ ID No. 23)
tgttgacagycvttcckggtATCCTGTCTGATGTGCAGCTTCAGGACTCAGGACCTGGTCTGGTG

AAACCTTCTCAGACAGTGTCCCTCACCTGCACTGTCACTGGCATCTCCATCACCACTGGAAATTT

CAGATGGAGCTGGATCCGGCAGTTTCCAGGAAACAAACTGGAGTGGATAGGGTACATATACTACA

GTGGTACCATTACCTACAATCCATCTCTCACAAGTCGAACCACCATCACTAGAGACACTTCCAAG

AACCAATTCTTCCTGGAAATGAACTCTTTGACTGCTGAAGACACAGCCACATACTACTGTGCACG

AGAACTCTACGGCTACGGGTACTTCGATGTCTGGGCCGCAGGGACCACGGTCACCGTCTCCTCAG

CTACAACAACAGCCCCATCTGTCTATCCCTTGGTCCCTGGCTGCAGTGACACATCTGGATCCTCG

GTGACACTGggatgccttgtcaaaggctagtcgactagtcg

ISK-MMH-TK1 L chain (amino acid sequence)
(SEQ ID No. 24)
LXFWIPASSSDVLMTQTPLSLPVSLGDQASISCRSSQSIVHSNGNTYLEWYLQKPGQSPKLLIYK

VSNRFSGVPDRFSGSGSGTDFTLKISRVEAEDLGVYYCFQGSHVPWTFGGGTKLEIKRADAAPTV

SIFPPVD*S

ISK-MMH-TK1 H chain (amino acid sequence)

(SEQ ID No. 25)
LLSXTXGVLSEVQLQQSGPELVKPGASVKISCKTSGYTFTKYTMHWVKQSHGKSLEWIGGINPNN

GGSRYDQKFRGKATLTVDKSSSTAYMEFRSLTSEDSAVYYCARDFVYWGQGTLVTVSAAKTTPPS

VYPLAPGSAAQTNSMVTLGCLVKG*STC

ISK-MMH-TK2 L chain (amino acid sequence)

(SEQ ID No. 26)
LXFWIPASSSDVVMTQIPLSLPVSLGDQASISCRSTQSLVHSNGNTYLHWFLQKPGQSPKLLIYK

VSNRFSGVPDRFSGSGSGTDFTLKISRVEAEDLGVYFCSQSKYVPRTFGGGTKLEIKRADAAPTV

SIFPPVD*S

ISK-MMH-TK2 H chain (amino acid sequence) → converted to amino acids from base 3 of the above DNA sequence.

(sequence No. 27)
LTXXXGILSDVQLQDSGPGLVKPSQTVSLTCTVTGISITTGNFRWSWIRQFPGNKLEWIGYIYYS

GTITYNPSLTSRTTITRDTSKNQFFLEMNSLTAEDTATYYCARELYGYGYEDVWAAGTTVTVSSA

TTTAPSVYPLVPGCSDTSGSSVTLGCLVKG*STS

ISK-MMH-TK1 (amino acid sequence of CDR)

(SEQ ID No. 1)
Heavy-chain CDR1: KYTMHG (SEQ ID No. 2)
Heavy-chain CDR2: INPNNGGSRYDQKFRG (SEQ ID No. 3)
Heavy-chain CDR3: DFVY (SEQ ID No. 4)
Light-chain CDR1: RSSQSIVHSNGNTYLE (SEQ ID No. 5)
Light-chain CDR2: KVSNRFS (SEQ ID No. 6)
Light-chain CDR3: FQGSHVP ISK-MMH-TK2 (amino acid sequence of CDR)

(SEQ ID No. 7)
Heavy-chain CDR1: TGNFRWS (SEQ ID No. 8)
Heavy-chain CDR2: YIYYS GTITYNPSLTS (SEQ ID No. 9)
Heavy-chain CDR3: RELYGYGYFDV (SEQ ID No. 10)
Light-chain CDR1: RSTQSLVHSNGNTYLH (SEQ ID No. 11)
Light-chain CDR2: KVSNRFS (SEQ ID No. 12)
Light-chain CDR3: SQSKYVP Note:
"X" is a portion corresponding to at least two bases (w = a or t, k = t or g, y = t or c, v = a, c, or g) of mixed primers.
Note:
"*" is a stop codon.

---

The invention claimed is:

1. A monoclonal antibody against a human HIG-1 polypeptide of the amino acid sequence of SEQ ID NO: 28, the antibody binding to an epitope within a region of SEQ ID NO: 28 from residue 1 to residue 19, wherein a heavy-chain variable region and a light-chain variable region have the following CDR:
   Heavy-chain CDR 1 consisting of the amino acid sequence of SEQ ID No. 1;
   Heavy-chain CDR 2 consisting of the amino acid sequence of SEQ ID No. 2;
   Heavy-chain CDR 3 consisting of the amino acid sequence of SEQ ID No. 3;
   Light-chain CDR 1 consisting of the amino acid sequence of SEQ ID No. 4;
   Light-chain CDR 2 consisting of the amino acid sequence of SEQ ID No. 5; and
   Light-chain CDR 3 consisting of the amino acid sequence of SEQ ID No. 6.

2. A monoclonal antibody against a human HIG-1 polypeptide of the amino acid sequence of SEQ ID NO: 28, the antibody binding to an epitope within a region of SEQ ID NO: 28 from residue 1 to residue 19, wherein a heavy-chain variable region and a light-chain variable region have the following CDR:
   Heavy-chain CDR 1 consisting of the amino acid sequence of SEQ ID No. 7;
   Heavy-chain CDR 2 consisting of the amino acid sequence of SEQ ID No. 8;
   Heavy-chain CDR 3 consisting of the amino acid sequence of SEQ ID No. 9;
   Light-chain CDR 1 consisting of the amino acid sequence of SEQ ID No. 10;
   Light-chain CDR 2 consisting of the amino acid sequence of SEQ ID No. 11; and
   Light-chain CDR 3 consisting of the amino acid sequence of SEQ ID No. 12.

3. An antibody fragment derived from the antibody according to claim 1 or 2, wherein the antibody fragment is Fab, Fab', F (ab')$_2$, Fv, or scFv.

4. The antibody according to claim 1 or 2, which is labeled or tagged.

5. The antibody fragment according to claim 3, which is labeled or tagged.

6. A cell line producing the monoclonal antibody according to claim 1 or 2.

7. A hybridoma having accession number FERM BP-11266 or FERM BP-11267.

8. A reagent for detecting a human HIG-1 polypeptide comprising the monoclonal antibody according to claim 1 or 2 or the antibody fragment derived from the monoclonal antibody.

9. A measurement kit comprising the reagent according to claim 8.

10. A test reagent to examine hypoxic, hypoglycemic, or ischemic conditions, comprising the monoclonal antibody according to claim 1 or 2 or the antibody fragment derived from the monoclonal antibody.

* * * * *

SEQUENCE LISTING

<160> NUMBER OF SEQ ID NOS: 28

<210> SEQ ID NO 1
<211> LENGTH: 6
<212> TYPE: PRT
<213> ORGANISM: Mus musculus

```
<400> SEQUENCE: 1

Lys Tyr Thr Met His Gly
1               5

<210> SEQ ID NO 2
<211> LENGTH: 16
<212> TYPE: PRT
<213> ORGANISM: Mus musculus

<400> SEQUENCE: 2

Ile Asn Pro Asn Asn Gly Gly Ser Arg Tyr Asp Gln Lys Phe Arg Gly
1               5                   10                  15

<210> SEQ ID NO 3
<211> LENGTH: 4
<212> TYPE: PRT
<213> ORGANISM: Mus musculus

<400> SEQUENCE: 3

Asp Phe Val Tyr
1

<210> SEQ ID NO 4
<211> LENGTH: 16
<212> TYPE: PRT
<213> ORGANISM: Mus musculus

<400> SEQUENCE: 4

Arg Ser Ser Gln Ser Ile Val His Ser Asn Gly Asn Thr Tyr Leu Glu
1               5                   10                  15

<210> SEQ ID NO 5
<211> LENGTH: 7
<212> TYPE: PRT
<213> ORGANISM: Mus musculus

<400> SEQUENCE: 5

Lys Val Ser Asn Arg Phe Ser
1               5

<210> SEQ ID NO 6
<211> LENGTH: 7
<212> TYPE: PRT
<213> ORGANISM: Mus musculus

<400> SEQUENCE: 6

Phe Gln Gly Ser His Val Pro
1               5

<210> SEQ ID NO 7
<211> LENGTH: 7
<212> TYPE: PRT
<213> ORGANISM: Mus musculus

<400> SEQUENCE: 7

Thr Gly Asn Phe Arg Trp Ser
1               5

<210> SEQ ID NO 8
<211> LENGTH: 16
<212> TYPE: PRT
<213> ORGANISM: Mus musculus

<400> SEQUENCE: 8
```

```
Tyr Ile Tyr Tyr Ser Gly Thr Ile Thr Tyr Asn Pro Ser Leu Thr Ser
1               5                   10                  15
```

<210> SEQ ID NO 9
<211> LENGTH: 11
<212> TYPE: PRT
<213> ORGANISM: Mus musculus

<400> SEQUENCE: 9

```
Arg Glu Leu Tyr Gly Tyr Gly Tyr Phe Asp Val
1               5                   10
```

<210> SEQ ID NO 10
<211> LENGTH: 16
<212> TYPE: PRT
<213> ORGANISM: Mus musculus

<400> SEQUENCE: 10

```
Arg Ser Thr Gln Ser Leu Val His Ser Asn Gly Asn Thr Tyr Leu His
1               5                   10                  15
```

<210> SEQ ID NO 11
<211> LENGTH: 7
<212> TYPE: PRT
<213> ORGANISM: Mus musculus

<400> SEQUENCE: 11

```
Lys Val Ser Asn Arg Phe Ser
1               5
```

<210> SEQ ID NO 12
<211> LENGTH: 7
<212> TYPE: PRT
<213> ORGANISM: Mus musculus

<400> SEQUENCE: 12

```
Ser Gln Ser Lys Tyr Val Pro
1               5
```

<210> SEQ ID NO 13
<211> LENGTH: 20
<212> TYPE: PRT
<213> ORGANISM: Artificial Sequence
<220> FEATURE:
<223> OTHER INFORMATION: Antigen

<400> SEQUENCE: 13

```
Cys Met Ser Thr Asp Thr Gly Val Ser Leu Pro Ser Tyr Glu Glu Asp
1               5                   10                  15

Gln Gly Ser Lys
            20
```

<210> SEQ ID NO 14
<211> LENGTH: 32
<212> TYPE: DNA
<213> ORGANISM: Artificial Sequence
<220> FEATURE:
<223> OTHER INFORMATION: Primer

<400> SEQUENCE: 14

```
cgactagtcg actggtggga agatggatac ag                              32
```

<210> SEQ ID NO 15
<211> LENGTH: 32
<212> TYPE: DNA
<213> ORGANISM: Artificial Sequence

```
<220> FEATURE:
<223> OTHER INFORMATION: Primer

<400> SEQUENCE: 15
cgacaagtcg actagcccctt gaccaggcat cc                              32

<210> SEQ ID NO 16
<211> LENGTH: 32
<212> TYPE: DNA
<213> ORGANISM: Artificial Sequence
<220> FEATURE:
<223> OTHER INFORMATION: Primer

<400> SEQUENCE: 16
cgactagtcg actagccttt gacaaggcat cc                               32

<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
ctgwtgttct ggattcctg                                              19

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
ctcctgtcak taactkcagg t                                           21

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
tgttgacagy cvttcckggt                                             20

<210> SEQ ID NO 20
<211> LENGTH: 417
<212> TYPE: DNA
<213> ORGANISM: Mus musculus

<400> SEQUENCE: 20
ctgwtgttct ggattcctgc ttccagcagt gatgttttga tgacccaaac tccactctcc    60
ctgcctgtca gtcttggaga tcaagcctcc atctcttgca gatctagtca gagcattgta   120
catagtaatg gaaacaccta tttagaatgg tacctgcaga aaccaggcca gtctccaaag   180
ctcctgatct acaaagtttc caaccgattt tctggggtcc cagacaggtt cagtggcagt   240
ggatcaggga cagatttcac actcaagatc agcagagtgg aggctgagga tctgggagtt   300
tattactgct ttcaaggttc acatgttccg tggacgttcg gtggaggcac caagctggaa   360
atcaaacggg ctgatgctgc accaactgta tccatcttcc caccagtcga ctagtcg      417

<210> SEQ ID NO 21
<211> LENGTH: 476
```

```
<210> SEQ ID NO 21
<211> LENGTH: 476
<212> TYPE: DNA
<213> ORGANISM: Mus musculus

<400> SEQUENCE: 21
ctcctgtcak taactkcagg tgtcctctct gaggtccagc tgcaacagtc tggacctgag    60
ctggtgaagc ctggggcttc agtgaagatt tcctgcaaga cttctggata cacattcact   120
aaatacacca tgcactgggt gaagcagagc catggaaaga gccttgagtg gattggaggt   180
attaatccta caatggtgg tagtaggtat gaccagaagt tcaggggcaa ggccacattg    240
actgtagaca gtcctccag cacagcctac atggagttcc gcagcctgac atctgaggat    300
tctgcagtct attactgtgc aagagacttt gtttactggg gccaagggac tctggtcact   360
gtctctgcag ccaaaacgac accccatct gtctatccac tggcccctgg atctgctgcc    420
caaactaact ccatggtgac cctgggatgc ctggtcaagg gctagtcgac ttgtcg       476

<210> SEQ ID NO 22
<211> LENGTH: 417
<212> TYPE: DNA
<213> ORGANISM: Mus musculus

<400> SEQUENCE: 22
ctgwtgttct ggattcctgc ttccagcagt gatgttgtga tgacccaaat tccactctcc    60
ctgcctgtca gtcttggaga tcaagcctcc atctcttgca gatctactca gagccttgta   120
cacagtaatg gaaacaccta tttacattgg ttcctgcaga agccaggcca gtctccaaag   180
ctcctgatct acaaagtttc caaccgattt tctggggtcc cagacaggtt cagtggcagt   240
ggatcaggga cagatttcac actcaagatc agccgagtgg aggctgagga tctgggagtt   300
tatttctgct ctcaaagtaa atatgttcct cggacgttcg gtggaggcac caagctggaa   360
atcaaacggg ctgatgctgc accaactgta tccatcttcc caccagtcga ctagtcg      417

<210> SEQ ID NO 23
<211> LENGTH: 496
<212> TYPE: DNA
<213> ORGANISM: Mus musculus

<400> SEQUENCE: 23
tgttgacagy cvttcckggt atcctgtctg atgtgcagct tcaggactca ggacctggtc    60
tggtgaaacc ttctcagaca gtgtccctca cctgcactgt cactggcatc tccatcacca   120
ctggaaattt cagatggagc tggatccggc agtttccagg aaacaaactg gagtggatag   180
ggtacatata ctacagtggt accattacct acaatccatc tctcacaagt cgaaccacca   240
tcactagaga cacttccaag aaccaattct tcctggaaat gaactctttg actgctgaag   300
acacagccac atactactgt gcacgagaac tctacggcta cgggtacttc gatgtctggg   360
ccgcagggac cacggtcacc gtctcctcag ctacaacaac agccccatct gtctatccct   420
tggtccctgg ctgcagtgac acatctggat cctcggtgac actgggatgc cttgtcaaag   480
gctagtcgac tagtcg                                                   496

<210> SEQ ID NO 24
<211> LENGTH: 137
<212> TYPE: PRT
<213> ORGANISM: Mus musculus
<220> FEATURE:
<221> NAME/KEY: UNSURE
<222> LOCATION: (2)..(2)
<223> OTHER INFORMATION: M or L.

<400> SEQUENCE: 24
```

```
Leu Xaa Phe Trp Ile Pro Ala Ser Ser Asp Val Leu Met Thr Gln
1               5                   10                  15

Thr Pro Leu Ser Leu Pro Val Ser Leu Gly Asp Gln Ala Ser Ile Ser
            20                  25                  30

Cys Arg Ser Ser Gln Ser Ile Val His Ser Asn Gly Asn Thr Tyr Leu
            35                  40                  45

Glu Trp Tyr Leu Gln Lys Pro Gly Gln Ser Pro Lys Leu Leu Ile Tyr
    50                  55                  60

Lys Val Ser Asn Arg Phe Ser Gly Val Pro Asp Arg Phe Ser Gly Ser
65                  70                  75                  80

Gly Ser Gly Thr Asp Phe Thr Leu Lys Ile Ser Arg Val Glu Ala Glu
            85                  90                  95

Asp Leu Gly Val Tyr Tyr Cys Phe Gln Gly Ser His Val Pro Trp Thr
            100                 105                 110

Phe Gly Gly Gly Thr Lys Leu Glu Ile Lys Arg Ala Asp Ala Ala Pro
            115                 120                 125

Thr Val Ser Ile Phe Pro Pro Val Asp
            130                 135

<210> SEQ ID NO 25
<211> LENGTH: 154
<212> TYPE: PRT
<213> ORGANISM: Mus musculus
<220> FEATURE:
<221> NAME/KEY: UNSURE
<222> LOCATION: (4)..(4)
<223> OTHER INFORMATION: V or L.
<220> FEATURE:
<221> NAME/KEY: UNSURE
<222> LOCATION: (6)..(6)
<223> OTHER INFORMATION: S or A.

<400> SEQUENCE: 25

Leu Leu Ser Xaa Thr Xaa Gly Val Leu Ser Glu Val Gln Leu Gln Gln
1               5                   10                  15

Ser Gly Pro Glu Leu Val Lys Pro Gly Ala Ser Val Lys Ile Ser Cys
            20                  25                  30

Lys Thr Ser Gly Tyr Thr Phe Thr Lys Tyr Thr Met His Trp Val Lys
            35                  40                  45

Gln Ser His Gly Lys Ser Leu Glu Trp Ile Gly Gly Ile Asn Pro Asn
    50                  55                  60

Asn Gly Gly Ser Arg Tyr Asp Gln Lys Phe Arg Gly Lys Ala Thr Leu
65                  70                  75                  80

Thr Val Asp Lys Ser Ser Ser Thr Ala Tyr Met Glu Phe Arg Ser Leu
            85                  90                  95

Thr Ser Glu Asp Ser Ala Val Tyr Tyr Cys Ala Arg Asp Phe Val Tyr
            100                 105                 110

Trp Gly Gln Gly Thr Leu Val Thr Val Ser Ala Ala Lys Thr Thr Pro
            115                 120                 125

Pro Ser Val Tyr Pro Leu Ala Pro Gly Ser Ala Ala Gln Thr Asn Ser
            130                 135                 140

Met Val Thr Leu Gly Cys Leu Val Lys Gly
145                 150

<210> SEQ ID NO 26
<211> LENGTH: 137
<212> TYPE: PRT
<213> ORGANISM: Mus musculus
<220> FEATURE:
```

```
<221> NAME/KEY: UNSURE
<222> LOCATION: (2)..(2)
<223> OTHER INFORMATION: M or L.

<400> SEQUENCE: 26

Leu Xaa Phe Trp Ile Pro Ala Ser Ser Ser Asp Val Val Met Thr Gln
1               5                   10                  15

Ile Pro Leu Ser Leu Pro Val Ser Leu Gly Asp Gln Ala Ser Ile Ser
            20                  25                  30

Cys Arg Ser Thr Gln Ser Leu Val His Ser Asn Gly Asn Thr Tyr Leu
        35                  40                  45

His Trp Phe Leu Gln Lys Pro Gly Gln Ser Pro Lys Leu Leu Ile Tyr
50                  55                  60

Lys Val Ser Asn Arg Phe Ser Gly Val Pro Asp Arg Phe Ser Gly Ser
65                  70                  75                  80

Gly Ser Gly Thr Asp Phe Thr Leu Lys Ile Ser Arg Val Glu Ala Glu
                85                  90                  95

Asp Leu Gly Val Tyr Phe Cys Ser Gln Ser Lys Tyr Val Pro Arg Thr
            100                 105                 110

Phe Gly Gly Gly Thr Lys Leu Glu Ile Lys Arg Ala Asp Ala Ala Pro
        115                 120                 125

Thr Val Ser Ile Phe Pro Pro Val Asp
    130                 135

<210> SEQ ID NO 27
<211> LENGTH: 160
<212> TYPE: PRT
<213> ORGANISM: Mus musculus
<220> FEATURE:
<221> NAME/KEY: UNSURE
<222> LOCATION: (3)..(3)
<223> OTHER INFORMATION: V or A.
<220> FEATURE:
<221> NAME/KEY: UNSURE
<222> LOCATION: (4)..(4)
<223> OTHER INFORMATION: L, I or V.
<220> FEATURE:
<221> NAME/KEY: UNSURE
<222> LOCATION: (5)..(5)
<223> OTHER INFORMATION: P.

<400> SEQUENCE: 27

Leu Thr Xaa Xaa Xaa Gly Ile Leu Ser Asp Val Gln Leu Gln Asp Ser
1               5                   10                  15

Gly Pro Gly Leu Val Lys Pro Ser Gln Thr Val Ser Leu Thr Cys Thr
            20                  25                  30

Val Thr Gly Ile Ser Ile Thr Thr Gly Asn Phe Arg Trp Ser Trp Ile
        35                  40                  45

Arg Gln Phe Pro Gly Asn Lys Leu Glu Trp Ile Gly Tyr Ile Tyr Tyr
50                  55                  60

Ser Gly Thr Ile Thr Tyr Asn Pro Ser Leu Thr Ser Arg Thr Thr Ile
65                  70                  75                  80

Thr Arg Asp Thr Ser Lys Asn Gln Phe Phe Leu Glu Met Asn Ser Leu
                85                  90                  95

Thr Ala Glu Asp Thr Ala Thr Tyr Tyr Cys Ala Arg Glu Leu Tyr Gly
            100                 105                 110

Tyr Gly Tyr Phe Asp Val Trp Ala Gly Thr Thr Val Thr Val Ser
        115                 120                 125

Ser Ala Thr Thr Thr Ala Pro Ser Val Tyr Pro Leu Val Pro Gly Cys
    130                 135                 140
```

```
Ser Asp Thr Ser Gly Ser Ser Val Thr Leu Gly Cys Leu Val Lys Gly
145                 150                 155                 160

<210> SEQ ID NO 28
<211> LENGTH: 93
<212> TYPE: PRT
<213> ORGANISM: Homo sapiens

<400> SEQUENCE: 28

Met Ser Thr Asp Thr Gly Val Ser Leu Pro Ser Tyr Glu Glu Asp Gln
1               5                   10                  15

Gly Ser Lys Leu Ile Arg Lys Ala Lys Glu Ala Pro Phe Val Pro Val
            20                  25                  30

Gly Ile Ala Gly Phe Ala Ala Ile Val Ala Tyr Gly Leu Tyr Lys Leu
            35                  40                  45

Lys Ser Arg Gly Asn Thr Lys Met Ser Ile His Leu Ile His Met Arg
    50                  55                  60

Val Ala Ala Gln Gly Phe Val Val Gly Ala Met Thr Val Gly Met Gly
65                  70                  75                  80

Tyr Ser Met Tyr Arg Glu Phe Trp Ala Lys Pro Lys Pro
                85                  90
```